(12) United States Patent
Park et al.

(10) Patent No.: US 12,251,412 B2
(45) Date of Patent: Mar. 18, 2025

(54) METHOD OF EXTRACTING CAFFEIC ACID AND ROSEMARINIC ACID FROM ROSEMARY

(71) Applicant: UCL CO. LTD., Jeju-si (KR)

(72) Inventors: Byoung Kwon Park, Incheon (KR); Jeong Mi Kim, Jeju-si (KR); Ji Young Moon, Jeju-si (KR); Min Jeong Kim, Jeju-si (KR); Mi So Moon, Jeju-si (KR); Jin Oh Park, Seoul (KR); Ji Won Lee, Seoul (KR)

(73) Assignee: UCL CO. LTD., Jeju-si (KR)

( * ) Notice: Subject to any disclaimer, the term of this patent is extended or adjusted under 35 U.S.C. 154(b) by 811 days.

(21) Appl. No.: 17/599,247

(22) PCT Filed: Aug. 10, 2020

(86) PCT No.: PCT/KR2020/010522
§ 371 (c)(1),
(2) Date: Sep. 28, 2021

(87) PCT Pub. No.: WO2021/040267
PCT Pub. Date: Mar. 4, 2021

(65) Prior Publication Data
US 2022/0143120 A1 May 12, 2022

(30) Foreign Application Priority Data
Aug. 29, 2019 (KR) .................. 10-2019-0106894

(51) Int. Cl.
*A61K 36/53* (2006.01)
*A23L 33/105* (2016.01)
(Continued)

(52) U.S. Cl.
CPC ............ *A61K 36/53* (2013.01); *A23L 33/105* (2016.08); *A61K 31/192* (2013.01);
(Continued)

(58) Field of Classification Search
None
See application file for complete search history.

(56) References Cited

U.S. PATENT DOCUMENTS

| 9,579,301 B2 | 2/2017 | Voelker et al. |
| 2003/0124204 A1 | 7/2003 | Sweet |

FOREIGN PATENT DOCUMENTS

| CN | 110025661 A | 7/2019 |
| JP | H09-67251 A | 3/1997 |

(Continued)

OTHER PUBLICATIONS

English language translation of JP 2884466 B2, Publ. Apr. 19, 1999. (Year: 1999).*

(Continued)

*Primary Examiner* — Dominic Lazaro
(74) *Attorney, Agent, or Firm* — WESTMAN CHAMPLIN & KOEHLER, P.A.; Amanda M. Prose

(57) ABSTRACT

The present disclosure relates to a method for extracting caffeic acid and rosmarinic acid from *Rosmarinus officinalis* L., and more particularly, to a method for extracting caffeic acid and rosmarinic acid from *Rosmarinus officinalis* L., the method comprising the steps of: (S1) preparing an extraction apparatus including an extractor for passing a solution contained in a main body unit through a filtration membrane to obtain a filtered solution, and dropping the filtered solution to the lower outside through a dropping unit connected to a lower portion of the main body unit, and a receiver located in the lower part of the extractor to collect the filtered solution that is dropped from the dropping unit; (S2) putting dried *Rosmarinus officinalis* L. into the main body unit, and adding a solvent to the main body unit to immerse the dried *Rosmarinus officinalis* L. at room temperature; and (S3) dropping a solution in which the dried *Rosmarinus*

(Continued)

*officinalis* L. has been immersed from the dropping unit to the receiver.

5 Claims, 2 Drawing Sheets

(51) Int. Cl.
  *A61K 31/192* (2006.01)
  *A61K 31/216* (2006.01)
  *B01D 11/02* (2006.01)
  *B01D 61/00* (2006.01)
(52) U.S. Cl.
  CPC ........ *A61K 31/216* (2013.01); *B01D 11/0288* (2013.01); *B01D 61/00* (2013.01); *A23V 2002/00* (2013.01); *A61K 2236/53* (2013.01)

(56) References Cited

FOREIGN PATENT DOCUMENTS

| | | | |
|---|---|---|---|
| JP | 2884466 B2 * | 4/1999 | |
| JP | 2002-281933 A | 10/2002 | |
| JP | 2005-132745 A | 5/2005 | |
| JP | 4845630 B2 * | 12/2011 | |
| JP | 5770428 B2 | 8/2015 | |
| KR | 10-0362885 B1 | 11/2002 | |
| KR | 10-2003-0082764 A | 10/2003 | |
| KR | 10-0606649 B1 | 7/2006 | |
| KR | 10-0697309 B1 | 3/2007 | |
| KR | 10-0729182 B1 | 6/2007 | |
| KR | 10-0971655 B1 | 7/2010 | |
| KR | 10-1161415 B1 | 7/2012 | |
| KR | 10-1205680 B1 | 11/2012 | |
| KR | 10-1205867 B1 | 11/2012 | |
| KR | 10-1236946 B1 | 2/2013 | |
| KR | 10-1454696 B1 | 10/2014 | |
| KR | 10-1513237 B1 | 4/2015 | |
| KR | 10-2015-0045259 A | 10/2015 | |
| KR | 10-1576232 B1 | 12/2015 | |
| KR | 10-1759776 B1 | 7/2017 | |
| KR | 10-2016-0096323 A | 12/2017 | |
| KR | 10-1981995 B1 | 9/2019 | |
| WO | 2012-060861 A1 | 5/2012 | |

OTHER PUBLICATIONS

English language translation of JP 4845630 B2, Publ. Dec. 28, 2011. (Year: 2011).*
Extended European Search Report issued for EP application Serial No. 20857590.2, dated Aug. 21, 2023.
International Search Report issued for PCT/KR2020/010522 dated Nov. 16, 2020.
Written Opinion of the International Searching Authority issued for PCT/KR2020/010522 dated Nov. 16, 2020.

* cited by examiner

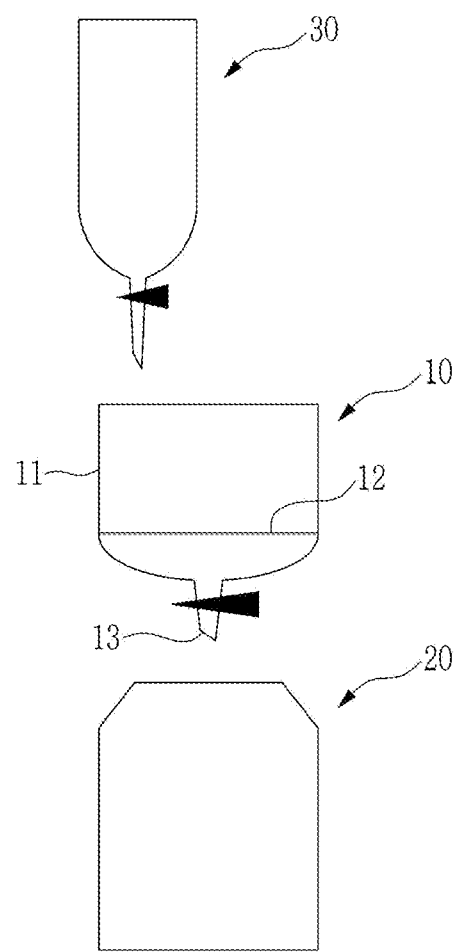

METHOD OF EXTRACTING CAFFEIC ACID AND ROSEMARINIC ACID FROM ROSEMARY

CROSS-REFERENCE TO RELATED APPLICATION

This Application is a Section 371 National Stage Application of International Application No. PCT/KR2020/010522 filed on Aug. 10, 2020, and published as WO 2021/040267 A1 on Mar. 4, 2021, in Korean, which claims priority to KR Patent Application Serial No. 10-2019-0106894 filed on Aug. 29, 2019, the contents of which are hereby incorporated by reference in their entirety.

BACKGROUND

1. Technical Field

The present disclosure relates to a method for extracting caffeic acid and rosmarinic acid from *Rosmarinus officinalis* L., and more particularly, to a method for extracting caffeic acid and rosmarinic acid from *Rosmarinus officinalis* L., the method which improves the extraction efficiency through an extraction process that is safe for the human body without loss of active ingredients.

The present application claims priority based on Korean Application No. 10-2019-0106894 filed on Aug. 29, 2019, and all contents disclosed in the specification of the corresponding application are incorporated in the present application by reference.

2. Description of Related Art

*Rosmarinus officinalis* L. is also called rosemary or Rosemary leaf whole, is a small evergreen shrub of Labiatae family whose leaves, shoots and flowers are edible, and is a temperate perennial plant native to southern Europe. It is a perennial plant with needle-like leaves, is a herb native to the Mediterranean coast, and has green leaves and a unique scent. Flowers bloom in winter and spring and have white, pink, purple, blue, and other colors. In particular, it is often used in meat dishes along with sage or thyme because the scent is preserved even when heat is applied. It is recommended to use less to preserve the flavor of the main dish as it has a strong aroma. The main ingredients of *Rosmarinus officinalis* L. include a wide variety of active ingredients such as alpha-pinene, apigenin, beta-carotene, beta-sitosterol, betulinic acid, borneol, coffee acid, caper, carnosol, carvacrol, carvone, caryophyllene, chlorogenic acid, diosmin, Genkwanin, geraniol, hesperidin, limonene, linalool, oleanolic acid, 1,8-cineole, rosmarinol, rosmarinic acid, caffeic acid, salicylic acid, squalene, tannin, thymol, ursolic acid, calcium, magnesium, manganese, phosphorus, potassium, zinc, vitamin B1, vitamin B3, vitamin C, etc., and a variety of application possibilities of *Rosmarinus officinalis* L. have been known as in antibacterial activity (KR 0729182 B1, KR 0362885 B1, KR 1161415 B1), antioxidant activity (KR 1205680 B1, KR 1205867 B1, KR 1454696 B1, KR 0606649 B1, KR 0971655 B1), whitening activity (KR 1513237 B1), atopic dermatitis reliever (Registered Patent No. 10-1236946), and antiviral activity (KR 0697309 B1, KR 2015-0045259 A).

In particular, the effects of caffeic acid such as anti-inflammatory, skin cancer reduction, oral cancer cell growth inhibition, etc. have been proven by many studies, and rosmarinic acid has been known to have a strong antioxidant effect, an anti-allergy effect, and effects in immunosuppression and atopy. Therefore, a method for extracting caffeic acid and rosmarinic acid from *Zostera marina* by adding an ionic eutectic solvent is disclosed in KR 1576232 B1.

However, there is still a need for research on an extraction method that can efficiently separate caffeic acid and rosmarinic acid while being safe for the human body.

SUMMARY

Accordingly, an object of the present disclosure is to provide a method for extracting caffeic acid and rosmarinic acid from *Rosmarinus officinalis* L., the method which improves the extraction efficiency through an extraction process that is safe for the human body without loss of active ingredients.

In order to achieve the above object, a method for extracting caffeic acid and rosmarinic acid from *Rosmarinus officinalis* L. according to the present disclosure comprises the steps of: (S1) preparing an extraction apparatus including an extractor for passing a solution contained in a main body unit through a filtration membrane to obtain a filtered solution, and dropping the filtered solution to the lower outside through a dropping unit connected to a lower portion of the main body unit, and a receiver located in the lower part of the extractor to collect the filtered solution that is dropped from the dropping unit; (S2) putting dried *Rosmarinus officinalis* L. into the main body unit, and adding a solvent to the main body unit to immerse the dried *Rosmarinus officinalis* L. at room temperature; and (S3) dropping a solution in which the dried *Rosmarinus officinalis* L. has been immersed from the dropping unit to the receiver.

At this time, the extraction apparatus in the step (S1) may further include a reservoir for replenishing a new solution in the main body unit by a decreased amount of the solution contained in the main body unit.

And, the solvent may include any one selected from the group consisting of $C_1$-$C_5$ monohydric alcohols, $C_2$-$C_5$ dihydric alcohols, and $C_3$-$C_5$ trihydric alcohols, or mixtures of two or more thereof.

At this time, the solvent may further include water.

Meanwhile, the method may further comprise, after the step (S3), a step of transferring the solution contained in the receiver to the main body unit.

Advantageous Effects

A method for extracting caffeic acid and rosmarinic acid from *Rosmarinus officinalis* L. according to the present disclosure can improve the extraction efficiency through an extraction process that is safe for the human body without loss of active ingredients due to heat during extraction of caffeic acid and rosmarinic acid from *Rosmarinus officinalis* L. by applying an extraction method in which a solution extracted is dropped from the top to the bottom.

BRIEF DESCRIPTION OF DRAWINGS

FIG. 3 is a view schematically showing an extraction apparatus for extracting caffeic acid and rosmarinic acid from *Rosmarinus officinalis* L., according to another embodiment of the present disclosure.

DESCRIPTION OF EXEMPLARY EMBODIMENTS

Hereinafter, embodiments of the present disclosure will be described in detail with reference to the accompanying drawings so that a person of ordinary skill in the art to which the present disclosure pertains can easily implement the embodiments of the present disclosure. However, the present disclosure may be embodied in various different forms and is not limited to the embodiments and drawings described herein.

The present disclosure has been completed by paying attention to the fact that a cold brew method of extracting with cold water for a long time even when extracting with the same coffee beans has a higher caffeine content and less bitter taste while researching a low-temperature extraction method in order to more safely and efficiently extract physiologically active ingredients of natural products that are weak to heat.

A method for extracting caffeic acid and rosmarinic acid from *Rosmarinus officinalis* L. according to an embodiment of the present disclosure will be described in detail with reference to the accompanying drawings.

Figure 1:
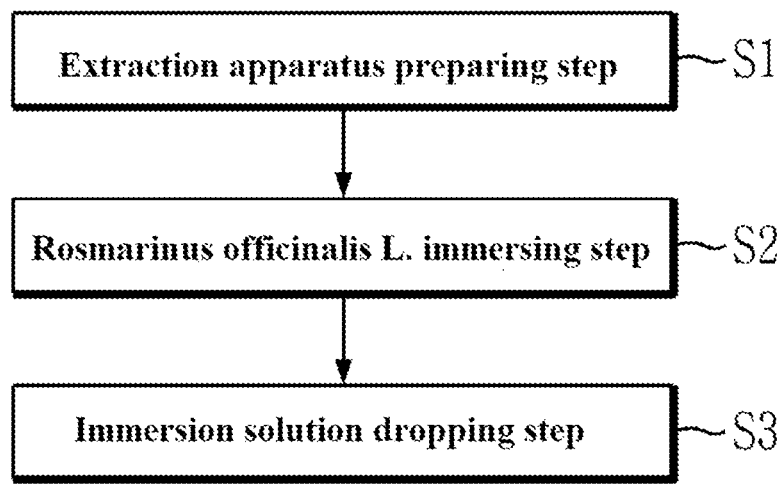
FIG. 1 is a view showing a process for extracting caffeic acid and rosmarinic acid from *Rosmarinus officinalis* L., according to an embodiment of the present disclosure.
Figure 2:
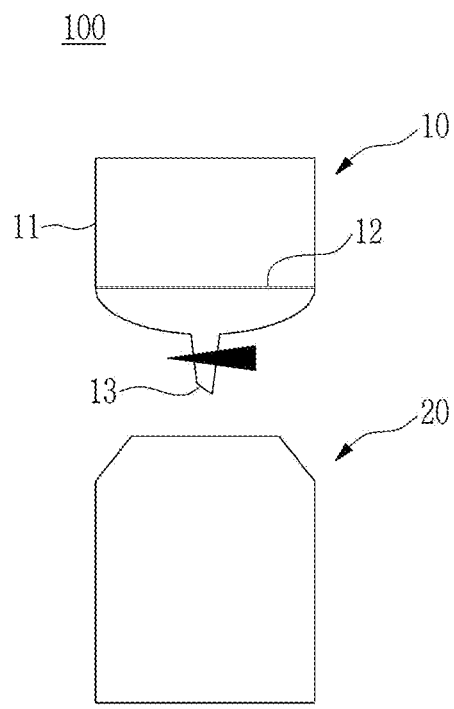
FIG. 2 is a view schematically showing an extraction apparatus for extracting caffeic acid and rosmarinic acid from *Rosmarinus officinalis* L., according to an embodiment of the present disclosure.

FIG. 1 is a view showing a process for extracting caffeic acid and rosmarinic acid from *Rosmarinus officinalis* L., according to an embodiment of the present disclosure, and FIGS. 2 and 3 are views schematically showing extraction apparatuses for extracting caffeic acid and rosmarinic acid from *Rosmarinus officinalis* L., according to embodiments of the present disclosure.

Referring to FIGS. 1 to 3, an extraction apparatus capable of extracting caffeic acid and rosmarinic acid from *Rosmarinus officinalis* L. is first prepared (step S1).

As can be seen in FIG. 2, the extraction apparatus 100 has an extractor 10 positioned in an upper part thereof, and a receiver 20 is positioned in a lower part of the extractor 10.

The extractor 10 passes a solution contained in a main body unit 11 through a filtration membrane 12 to obtain a filtered solution, and drops the filtered solution to the lower outside through a dropping unit 13 connected to a lower portion of the main body unit 11.

The extractor 10 is a reactor for extracting active ingredients from the solid by containing a solid such as dried *Rosmarinus officinalis* L., *Rosmarinus officinalis* L. powder, or the like and a solvent together, and includes a filtration membrane 12 capable of preventing loss of the solid and filtering the extracted solution. Preferably, a stopcock valve is located in the dropping unit 13 to enable the dropping speed of the filtered solution containing the active ingredients to be adjusted.

The receiver 20 is located in the lower part of the extractor 10 and is for collecting the filtered solution containing the active ingredients of *Rosmarinus officinalis* L. dropped from the dropping unit 13, and the types of the receiver is not limited.

Further, it is important to constantly maintain the amount of an extraction solvent in order to increase the extraction efficiency of a raw material in the main body unit 11, and it is good to continuously replenish a new solution to the main body unit 11 by the amount of the solution decreased when the solution that contains the active ingredients and is contained in the main body unit 11 is discharged to the bottom. For this purpose, a reservoir 30 capable of storing the new solvent may be further included, and the reservoir 30 may be positioned above the extractor 10 as can be seen in FIG. 3. It is preferably for the reservoir 30 to include a stopcock valve so as to control the dropping speed of the new solvent.

Subsequently, the dried *Rosmarinus officinalis* L. is put into the main body unit 11, and a solvent is added to the main body unit 11 to immerse the dried *Rosmarinus officinalis* L. at room temperature (step S2).

The dried *Rosmarinus officinalis* L. may be cut to a predetermined size or may be powdered in order to increase the extraction efficiency.

When extracting the dried *Rosmarinus officinalis* L., the extraction efficiency of caffeic acid and rosmarinic acid can be increased by putting *Rosmarinus officinalis* L. and a solvent in the main body unit 11 and immersing *Rosmarinus officinalis* L. at room temperature.

Here, immersion is for impregnating the solvent in the cell membrane of a dried raw material, that is, soaking the raw material, and it is much more efficient to perform extraction after immersion than to perform extraction immediately in a dried state.

Further, the solvent may be alcohols, and more specifically, it may include any one selected from the group consisting of $C_1$-$C_5$ monohydric alcohols, $C_2$-$C_5$ dihydric alcohols, and $C_3$-$C_5$ trihydric alcohols, or mixtures of two or more thereof.

Although the monohydric alcohols may be methanol, ethanol, propanol, isopropanol, butanol, t-butanol and pentanol, the dihydric alcohols may be ethylene glycol, propylene glycol, butylene glycol, and pentylene glycol, and the trihydric alcohols may be glycerol, the types thereof are not limited.

When dihydric alcohols and trihydric alcohols except ethanol were used alone, caffeic acid and rosmarinic acid have not been detected at all in the case of performing extraction by a conventional room temperature immersion method for 24 hours, but remarkably higher amounts of caffeic acid and rosmarinic acid have been detected in the case of performing extraction by the method according to the present disclosure.

Further, caffeic acid and rosmarinic acid have not been detected at all even if stirring was performed when the solvent was water, or when the content of water in the solvent was more than half, for example, 80% by weight or more in the case of performing extraction by the conventional room temperature immersion method. However, large amounts of caffeic acid and rosmarinic acid have been detected when a solvent obtained by mixing water and the alcohols was used, and even when the content of water in the solvent was more than half, for example, 80% by weight or more in the case of performing extraction by the method according to the present disclosure.

Subsequently, a solution in which the dried *Rosmarinus officinalis* L. is immersed is dropped from the dropping unit 13 to the receiver 20 (step S3).

When the dried *Rosmarinus officinalis* L. sufficiently contains an extraction solvent, the solution is dropped into the receiver through the dropping unit 13 located at the lower portion of the extractor 10. At this time, the dropping solution is collected in the receiver by performing dropping extraction while adjusting the dropping speed by opening the stopcock valve located in the dropping unit 13.

At this time, the dropping extraction may be performed again by transferring the solution contained in the receiver 20 to the main body unit 11 after the step (S3). The solution contained in the receiver 20 may be transferred to the main body unit 11, and may further be transferred even to the reservoir 30. The extraction efficiency of caffeic acid and rosmarinic acid can be further increased through such a process.

As described above, a method for extracting caffeic acid and rosmarinic acid from *Rosmarinus officinalis* L. according to the present disclosure is a very efficient method for extracting caffeic acid and rosmarinic acid through alcohols or a mixed solvent of the alcohols and water while minimizing loss of active ingredients weak to heat by performing extraction at room temperature.

Hereinafter, the present disclosure will be described in more detail through specific Examples. The following Examples are intended to illustrate the present disclosure, but the present disclosure is not limited by the following Examples.

Example: Dropping Extraction

As an extractor for passing a solution contained in the main body unit through the filtration membrane to obtain a filtered solution, and dropping the filtered solution to the lower outside through the dropping unit connected to the lower portion of the main body unit, an extractor capable of adjusting the dropping speed of the solution was installed in the upper part, and a receiver for collecting the filtered solution dropped from the dropping unit of the extractor was installed in the lower part of the extractor.

After putting 50 g of dried *Rosmarinus officinalis* L. and 950 g of each solvent shown in Table 2 into the main body unit of the prepared extractor, and immersing the dried *Rosmarinus officinalis* L. in the solvent at room temperature for 1 hour so that the dried *Rosmarinus officinalis* L. could sufficiently absorb the solvent, an extract was obtained by slowly dropping the solution of the extractor into the receiver in the lower part for 30 minutes.

For reference, the extracted extract was extracted once more (extracted twice) by injecting an extract extracted in Example 5c into the extractor again in Example 6a of Table 2 below, and the extracted extract was extracted one more time (extracted three times) by injecting an extract extracted in Example 6a into the extractor again in Example 6b.

Comparative Example: Immersion Extraction

After putting 50 g of dried *Rosmarinus officinalis* L. and 950 g of each solvent shown in Table 2 below into a general container and immersing the dried *Rosmarinus officinalis* L. in the solvent at room temperature for 24 hours, a *Rosmarinus officinalis* L. extract was obtained by performing filtration.

Experimental Example: Analysis of Extract Ingredients

The contents of ingredients were checked depending on the following analysis conditions.

After dissolving standard products of caffeic acid and rosmarinic acid in an HPLC mobile phase to prepare a solution with a concentration of 100 ppm, a standard solution was prepared by filtering the solution with a PVDF membrane filter having a thickness of 0.45 μm.

Sample solutions of Examples and Comparative Examples were prepared by filtering undiluted solutions of *Rosmarinus officinalis* L. extracts (immersion extraction and dropping extraction) with a filter having a thickness of 0.45 μm, analysis was carried out depending on the following HPLC analysis conditions, and the results are shown in Table 2.

1. Analysis Equipment
   High Performance Liquid Chromatography (Waters 2695, 2998 PDA detector)
2. Analysis Conditions
   (1) column: C18, 4.6*250 mm, 5 μm
   (2) flow: 1 ml/min
   (3) injection volume: 10 μl
   (4) detection: 327 nm (rosmarinic acid), 323 nm (caffeic acid)
   (5) Mobile phase

TABLE 1

| Time(min) | A(0.1% acetic acid in water) | B(acetonitrile) |
|---|---|---|
| 0 | 80 | 20 |
| 40 | 30 | 70 |
| 45 | 0 | 100 |
| 50 | 80 | 20 |
| 60 | 80 | 20 |

(6) Standard: rosmarinic acid, caffeic acid

The ingredients of Examples and Comparative Examples shown in Table 2 below were analyzed depending on the analysis conditions, and the results are shown in Table 2 below.

TABLE 2

| Classification | Solvent | Ratio | Extraction method | Rosmarinic acid (ppm) | Caffeic acid (ppm) |
|---|---|---|---|---|---|
| Comparative Example 1 | Water | | Immersion extraction | 0 | 0 |
| Comparative Example 2 | Ethanol | | Immersion extraction | 16 | 5 |
| Comparative Example 3 | Water + ethanol | 20:80 | Immersion extraction | 20 | 6 |
| Comparative Example 4 | Water + propanediol | 80:20 | Immersion extraction | 0 | 0 |
| Example 1 | Ethanol | | Dropping extraction | 30 | 10 |
| Example 2 | Glycerin | | Dropping extraction | 10 | 3 |
| Example 3 | Butylene Glycol | | Dropping extraction | 15 | 2 |
| Example 4 | Water + ethanol | 20:80 | Dropping extraction | 55 | 10 |
| Example 5a | Water + propanediol | 20:80 | Dropping extraction | 20 | 3 |
| Example 5b | Water + propanediol | 50:50 | Dropping extraction | 16 | 4 |
| Example 5c | Water + propanediol | 80:20 | Dropping extraction | 14 | 4 |
| Example 6a | Water + propanediol | 80:20 | Dropping extraction | 23 | 6 |
| Example 6b | Water + propanediol | 80:20 | Dropping extraction | 60 | 10 |

Looking at Table 2 above, extraction contents of caffeic acid and rosmarinic acid are higher in the case of performing extraction by the dropping extraction method according to the present disclosure when the same solvent is used if Comparative Examples 2 to 4 using a general immersion extraction method are compared with Examples 1, 4, and 5c using a dropping extraction method according to the present disclosure. Caffeic acid and rosmarinic acid were not extracted in Comparative Example 4 which is the general immersion extraction method, whereas significant amounts of caffeic acid and rosmarinic acid were extracted in Example 5c using the same solvent, and it can be confirmed that the dropping extraction method is a very effective method compared to the general immersion extraction method.

Further, although caffeic acid and rosmarinic acid were not extracted at all in the case of Comparative Example 1 in which *Rosmarinus officinalis* L. was immersed in water as a solvent and in the case of Comparative Example 4 in which immersion extraction were performed using a solvent having a content of water as the solvent of 80% by weight, it can be confirmed that the dropping extraction method according to the present disclosure is a very effective method considering that significant amounts of caffeic acid and rosmarinic acid were extracted even if the ratios of water were high in Examples 5b and 5c.

Further, looking at Examples 5a to 5c in which use amounts of water and alcohols were compared, the contents of caffeic acid were not decreased at all, but rather showed an increasing trend, even if the contents of water were increased.

Furthermore, looking at Examples 6a and 6b in which the extraction step was repeated with respect to the extract extracted in Example 5c, it can be confirmed that the contents of caffeic acid and rosmarinic acid are remarkably increased as the number of extractions is increased.

Therefore, it can be seen that the dropping extraction method according to the present disclosure is very effective in extracting caffeic acid and rosmarinic acid from *Rosmarinus officinalis* L.

The above description merely exemplarily describes the present disclosure, and a person of ordinary skill in the art to which the present disclosure pertains will be able to understand that the present disclosure may be implemented in a modified form within a range that does not depart from the essential characteristics of the present disclosure. Therefore, the disclosed Examples and Experimental Examples should be considered in an explanatory point of view rather than a limited point of view. The scope of the present disclosure is indicated in the patent claim scope rather than the foregoing description, and all differences within the scope equivalent thereto should be construed as being included in the present disclosure.

EXPLANATION OF MARKS

10: Extractor
11: Main body unit
12: Filtration membrane
13: Dropping unit
20: Receiver
30: Reservoir
100: Extraction apparatus

What is claimed is:

1. A method for extracting caffeic acid and rosmarinic acid from *Rosmarinus officinalis* L., the method comprising the steps of:
   (S1) preparing an extraction apparatus including an extractor for passing a solution contained in a main body unit through a filtration membrane to obtain a filtered solution, and dropping the filtered solution to the lower portion through a dropping unit connected to a lower portion of the main body unit, and a receiver located in the lower portion of the extractor to collect the filtered solution that is dropped from the dropping unit;
   (S2) putting dried *Rosmarinus officinalis* L. into the main body unit, and adding a solvent to the main body unit to immerse the dried *Rosmarinus officinalis* L. at room temperature; and
   (S3) dropping a solution in which the dried *Rosmarinus officinalis* L. has been immersed from the dropping unit to the receiver in order to obtain an extract comprising caffeic acid and rosmarinic acid.

2. The method of claim 1, wherein the extraction apparatus in the step (S1) further includes a reservoir for replenishing a new solution in the main body unit by a decreased amount of the solution contained in the main body unit.

3. The method of claim 1, wherein the solvent includes any one selected from the group consisting of C 1-C 5 monohydric alcohols, C 2-C 5 dihydric alcohols, and C 3-C 5 trihydric alcohols, or mixtures of two or more thereof.

4. The method of claim 3, wherein the solvent further includes water.

5. The method of claim 1, further comprising, after the step (S3), a step of transferring the solution contained in the receiver to the main body unit.

* * * * *